(12) United States Patent
Kawakatsu et al.

(10) Patent No.: US 8,236,913 B2
(45) Date of Patent: Aug. 7, 2012

(54) (METH)ACRYLATE COPOLYMER, A METHOD FOR PRODUCING THE SAME AND A MEDICAL DEVICE

(75) Inventors: Yuta Kawakatsu, Ohtsu (JP); Susumu Kashiwabara, Ohtsu (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 317 days.

(21) Appl. No.: 12/517,521

(22) PCT Filed: Dec. 7, 2006

(86) PCT No.: PCT/JP2006/324427
§ 371 (c)(1),
(2), (4) Date: Jun. 3, 2009

(87) PCT Pub. No.: WO2008/068868
PCT Pub. Date: Jun. 12, 2008

(65) Prior Publication Data
US 2010/0069595 A1    Mar. 18, 2010

(51) Int. Cl.
C08F 220/18 (2006.01)
C08F 118/02 (2006.01)
C08F 220/10 (2006.01)
(52) U.S. Cl. .................. 526/329.6; 526/319; 526/318.4
(58) Field of Classification Search ............... 526/329.6, 526/319, 318.4
See application file for complete search history.

(56) References Cited

U.S. PATENT DOCUMENTS

| 2002/0064558 A1 | 5/2002 | Tanaka et al. | |
|---|---|---|---|
| 2003/0153964 A1* | 8/2003 | Al-Lamee et al. | 607/115 |

FOREIGN PATENT DOCUMENTS

| JP | 01-168703 A | 7/1989 |
| JP | 03-095229 A | 4/1991 |
| JP | 03-055482 B2 | 8/1991 |
| JP | 03-505471 A | 11/1991 |
| JP | 05-132521 A | 5/1993 |
| JP | 06-503114 A | 4/1994 |
| JP | 08-266895 A | 10/1996 |
| JP | 09-067153 A | 3/1997 |
| JP | 10-131089 A | 5/1998 |
| JP | 11-035605 A | 2/1999 |
| JP | 11-171927 A | 6/1999 |
| JP | 11-279083 A | 10/1999 |
| JP | 11-287802 A | 10/1999 |
| JP | 11279083 A * | 10/1999 |
| JP | 11-335647 A | 12/1999 |
| JP | 11335647 A * | 12/1999 |
| JP | 2001-172068 A | 6/2001 |
| JP | 2002-105136 A | 4/2002 |
| JP | 2002-187755 A | 7/2002 |
| JP | 2004-161954 A | 6/2004 |
| JP | 3741320 B2 | 11/2005 |
| JP | 2006-077136 A | 3/2006 |
| JP | 2006-124714 A | 5/2006 |
| JP | 2006-299045 A | 11/2006 |
| JP | 2006299045 A * | 11/2006 |
| WO | WO 90/03406 A1 | 4/1990 |
| WO | WO 92/09639 A2 | 6/1992 |
| WO | WO 97/04756 A2 | 2/1997 |
| WO | WO 01/66171 A1 | 9/2001 |
| WO | WO 03/106518 A1 | 12/2003 |

OTHER PUBLICATIONS

Andrade et al., *Trans. Am. Soc. Artif. Intern. Organs*, 75-84 (1987).
Matsuda et al., *Jpn. J. Artif. Organs*, 16(2): 1045-1050 (1987).
Niu et al., *Jpn. J. Artif. Organs*, 19(3): 1287-1291 (1990).
Takemoto et al., *Medical Polymer* (Mita Press, 1989), pp. 72-73.

* cited by examiner

*Primary Examiner* — Michael M Bernshteyn
(74) *Attorney, Agent, or Firm* — Leydig, Voit & Mayer, Ltd.

(57) ABSTRACT

[Object] An object of the present invention is to provide a surface-treating agent excellent in antithrombogenicity, and accordingly, excellent in biocompatibility, and having high hydrophilicity as compared with conventional medical materials. Further, an object of the present invention is to provide a production method excellent in performance of removing unreacted monomers and further improving a yield as compared with conventional production methods.

[Constitution] The present invention relates to a water-insoluble copolymer comprising alkyl(meth)acrylate and methoxypolyethylene glycol(meth)acrylate. The present invention also relates to a method for producing a water-insoluble (meth)acrylate copolymer by copolymerizing alkyl (meth)acrylate and methoxypolyethylene glycol(meth)acrylate in a common polymerization solvent. Further, the present invention relates to a method for purifying (meth)acrylate copolymer by purifying (meth)acrylate copolymer by reprecipitation using a mixed solution of an alcohol having 1 to 10 carbon atoms and water.

11 Claims, 4 Drawing Sheets

[Fig. 1]
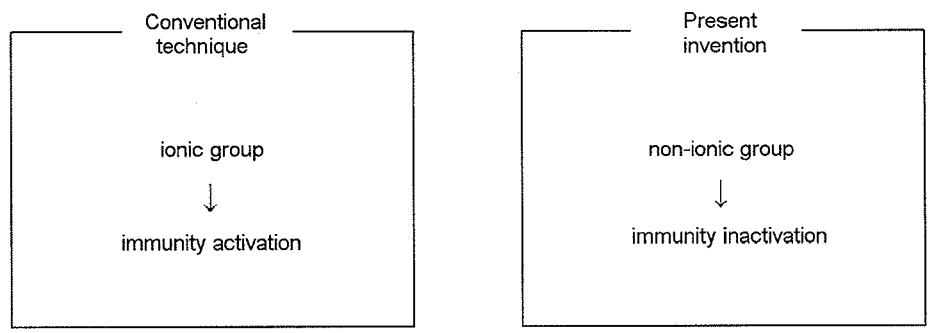
[Fig. 2]
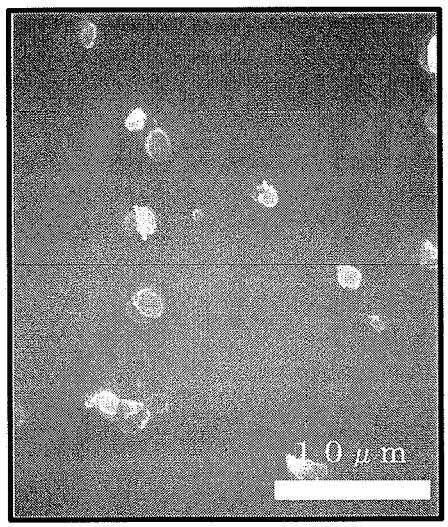
[Fig. 3]
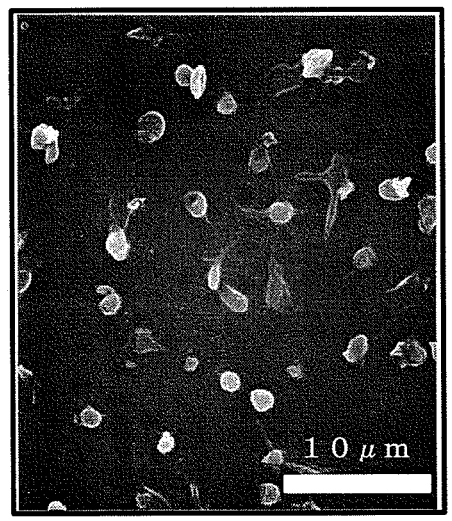

[Fig. 4]
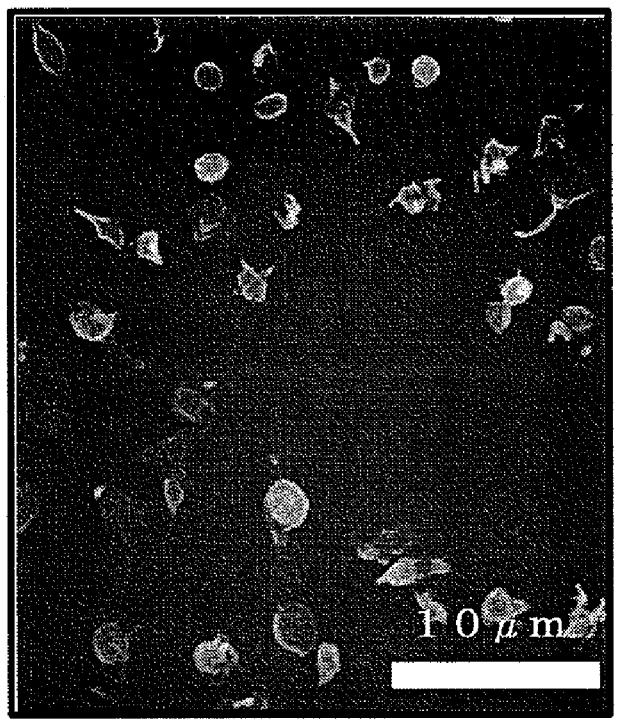
[Fig. 5]
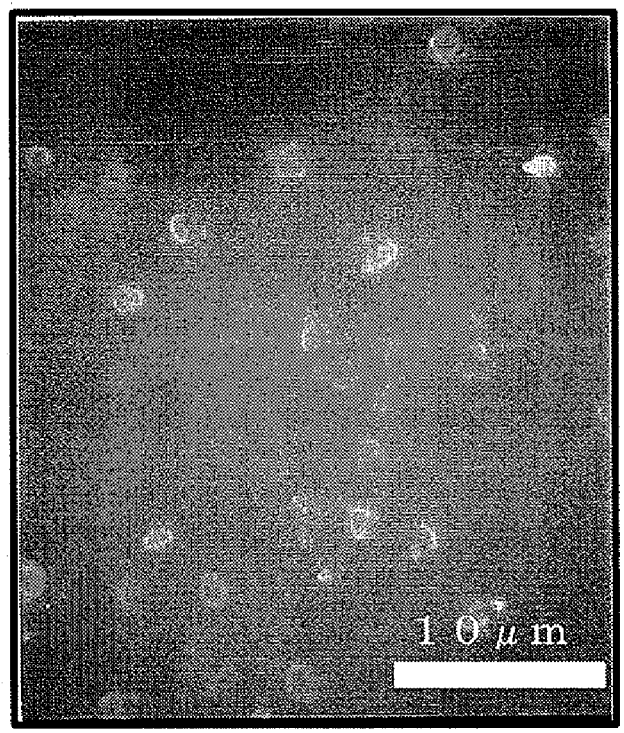

[Fig. 6]
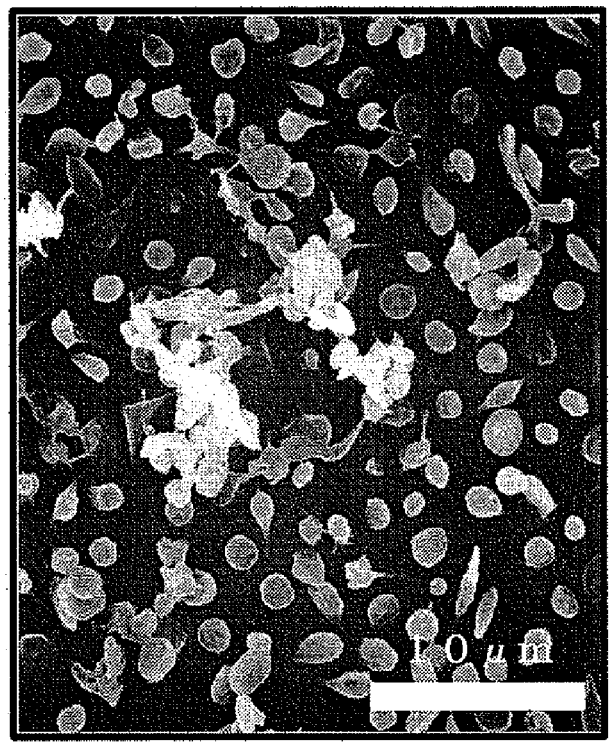
[Fig. 7]
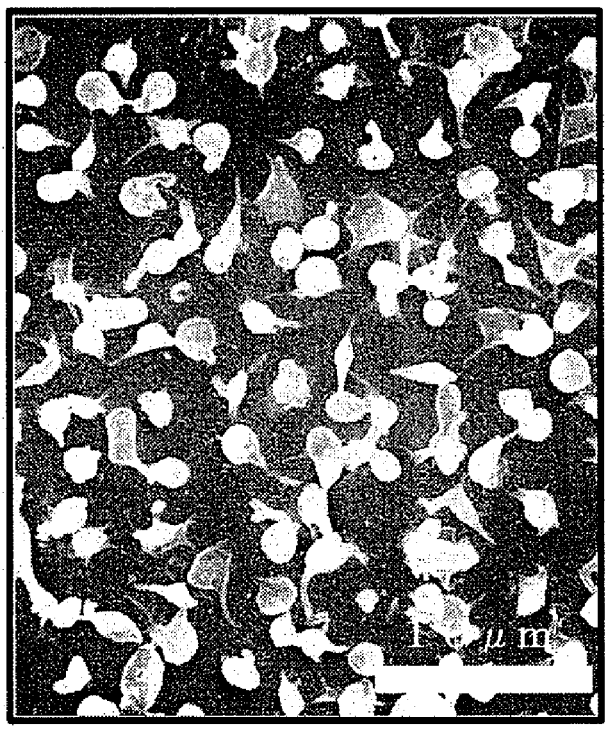

[Fig. 8]
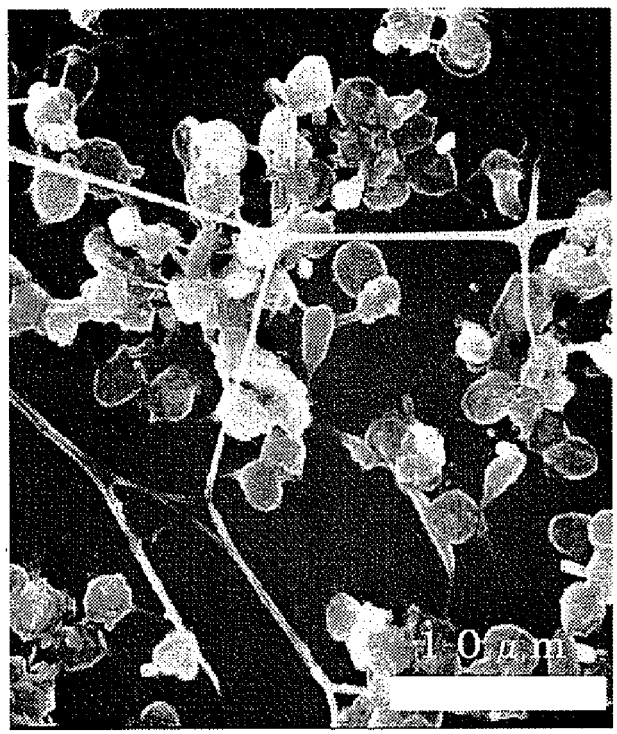
[Fig. 9]
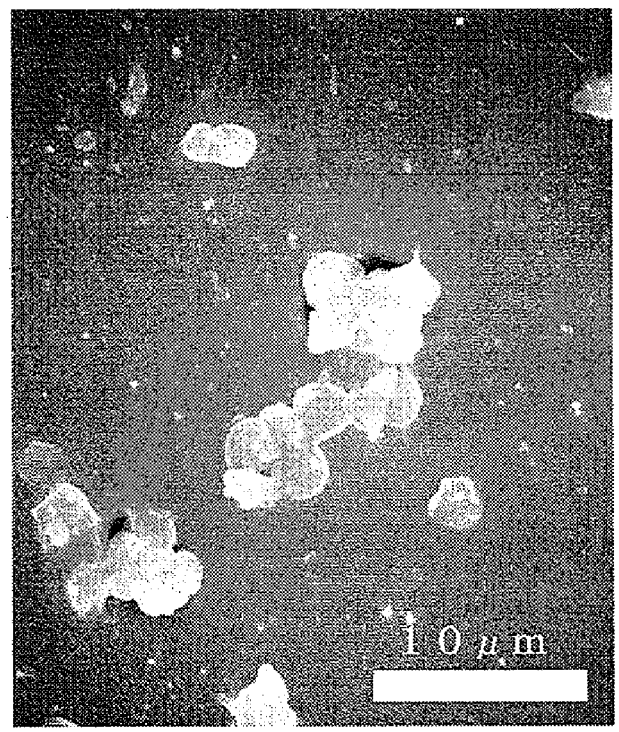

(METH)ACRYLATE COPOLYMER, A METHOD FOR PRODUCING THE SAME AND A MEDICAL DEVICE

TECHNICAL FIELD OF THE INVENTION

The present invention relates to a copolymer imparting blood compatibility to a medical device. The present invention also relates to a method for producing a (meth)acrylate copolymer, and in particular, relates to a method for producing a water-insoluble (meth)acrylate copolymer obtained by copolymerizing a hydrophilic (meth)acrylate monomer and a hydrophobic (meth)acrylate monomer at a specific molar ratio.

BACKGROUND ART

In recent years, studies on medical materials utilizing various polymer materials have been progressed, and application to a blood filter, an artificial kidney membrane, a plasma separation membrane, a catheter, an artificial lung membrane, an artificial blood vessel, an adhesion-proof membrane, an artificial skin, and the like have been expected. Since this case results in using a synthetic material that is a foreign matter for a living body by bringing it in contact with tissues in a living body and blood, it is required for the medical material to have biocompatibility.

When the medical material is used as a material being in contact with blood, three elements including (a) suppression of the blood coagulation system, (b) suppression of adhesion and activation of platelets and (c) suppression of activation of the complement system become important points for biocompatibility. In particular, in the case of using the medical material as a material being in contact with blood for a comparatively short time such as an extracorporeal circulation medical material (for example, artificial kidney and plasma separation membrane), generally, for simultaneously using an anticoagulant such as heparin or sodium citrate, suppression of activation of platelets and the complement system of the above described (b) and (c) is a particularly important object.

Regarding (b) suppression of adhesion and activation of platelets, it is considered that a micro phase-separated surface, or a hydrophilic surface, particularly, a gelled surface with which a water-soluble polymer is combined is excellent, and a hydrophobic surface such as that of polypropylene is said to be inferior (Nonpatent Documents 1 and 2). However, although a surface having a micro phase separation structure makes it possible to exhibit good blood compatibility by controlling the surface itself to an appropriate phase separated state, conditions capable of producing such phase separation are limited and there is a restriction on applications thereof. Further, in a gelled surface with which a water-soluble polymer is combined, although adhesion of platelets is suppressed, platelets activated on a material surface and small thrombus are returned to a body, and variation of abnormal blood cell components (platelets) are frequently observed, which may cause a problem.

On the other hand, (c) regarding activation of the complement system, it is known that a surface having a hydroxyl group such as cellulose or an ethylene-vinyl alcohol copolymer has high activity, and a hydrophobic surface such as that of polypropylene has slight activity (Nonpatent Document 3). Therefore, when a cellulose-based or vinyl alcohol-based material is used in, for example, an artificial organ membrane, a problem of activation of the complement system is caused, and on the contrary, when a hydrophobic surface such as that of polyethylene is used, a problem of adhesion and activation of platelets is caused.

Further, in the case of using the medical material as a material being in contact with blood for a comparatively long time, for example, such as an artificial blood vessel, in addition to the above described three elements, in order to preferably carry out neointimal formation and regeneration and reproduction of tissues in a living body, it is necessary to use a material having an affinity for tissues (cells) in a living body. As such a material of an artificial blood vessel, for example, an artificial blood vessel made of a super-micro polyester fiber is known (Nonpatent Document 4). This super-micro polyester fiber is one of medical materials utilizing recognition of foreign matters in a living body, wound healing by biological defense, and self tissue reproduction, and is mainly used as an artificial blood vessel at present. However, long term application of this artificial blood vessel to a fine blood vessel causes a problem of occluding the artificial blood vessel.

Further, for medical devices being in contact with tissues in a living body or a biological fluid other than blood, for example, adhesion preventing membranes and implant materials that are used by being embedded in a living body for a long time, or wound dressing materials used in contact with wounds (regions of injury caused by peeling of a skin and exposition of a living tissue), it is required to have a surface with less recognition of foreign matters in a living body and easily separating from the living body (non-adhesive surface). However, since tissues in a living body are adhered to a material surface in the cases of silicone, polyurethane and polytetrafluoroethylene conventionally used as the above described materials, recognition of foreign matters in a living body is too strong, and thus, satisfactory performance could not be obtained.

Another medical material is polyethylene glycol (PEG). PEG has significantly excellent blood compatibility, and many application studies for the medical field have been made. However, since PEG is water-soluble, in the case of being used as a medical material, PEG has been required to be formed into a block copolymer or a graft copolymer with other polymers and fixed to a material surface.

Further, a technique of exhibiting antithrombogenicity by coating a surface being in contact with blood with poly(2-methoxyethyl acrylate) that is a biocompatible material has been known (Patent Document 1). However, since the material dissolves in methanol but insoluble in ethanol, toxicity of a solvent remaining in a substrate after coating is concerned.

Further, a water-soluble copolymer of polyethylene glycol acrylate and alkyl acrylate has been known (Patent Document 2). With this technique, protection of a surface of a solid phase can be performed in immunoassay. However, since this copolymer is water-soluble, long-term maintenance of biocompatibility is difficult.

Furthermore, a phosphorylcholine analog group-containing polymer has been known (Patent Document 3). This technique allows a phosphorylcholine analog group-containing polymer to be water-insoluble while maintaining good biocompatibility by copolymerizing a hydrophilic (meth)acrylate monomer (hereinafter referred to as MPC) containing a phosphorylcholine group, which has high biocompatibility, and an alkyl(meth)acrylate monomer having high hydrophobicity. However, since this copolymer is in a rigid solid state, there is not only a possibility of separation of a film after coating, but also insufficiency of biocompatibility from the viewpoint of immunity. It is considered that an ammonium ion (N+) contained in a phosphorylcholine group activates the immune system in a living body (see FIG. 1).

(Nonpatent Documents)
1. Trans. Am. Soc. Artif. Intern. Organs, vol. XXXIII, p. 75-84 (1987)
2. Polymer and Medical Treatment, Mita Publishing Company, p. 72-73 (1989)
3. Jinkou Zouki, 16(2), p. 1045-1050 (1987)
4. Jinkou Zouki, 19(3), p. 1287-1291 (1990)

(Patent Documents)
1. Japanese Patent Application Laid-Open (JP-A) No. 2002-105136
2. Japanese Patent Application Laid-Open (JP-A) No. 287802/99
3. Japanese Patent Application Laid-Open (JP-A) No. 35605/99

As a method for producing the copolymer of polyethylene glycol acrylate and alkyl acrylate, reprecipitation is most conveniently used. Herein, reprecipitation refers to a technique of repeatedly generating precipitates to enhance the purity, and is performed for the purpose of removing low molecular weight compounds (such as monomers) in polymer synthesis. However, since two types of monomers being hydrophilic and hydrophobic are used in the present invention, selection of a poor solvent used in reprecipitation is important. That is, this is because that an ability of dissolving both of the monomers having different properties and precipitating only the obtained copolymer is to be required. However, it has been difficult that a sieve of such a subtle dissolving property is exhibited with one solvent.

BRIEF DESCRIPTIONS OF DRAWINGS

FIG. 1 is a schematic view indicating differences between the present invention and a conventional technique.
FIG. 2 is an SEM image indicating a result of the blood compatibility test using a purified product 1 of Example 1.
FIG. 3 is an SEM image indicating a result of the blood compatibility test using a purified product 4 of Example 4.
FIG. 4 is an SEM image indicating a result of the blood compatibility test using a purified product 5 of Example 5.
FIG. 5 is an SEM image indicating a result of the blood compatibility test using a purified product 6 of Example 6.
FIG. 6 is an SEM image indicating a result of the blood compatibility test using a purified product 9 of Comparative Example 3.
FIG. 7 is an SEM image indicating a result of the blood compatibility test using a purified product 10 of Comparative Example 4.
FIG. 8 is an SEM image indicating a result of the blood compatibility test using a purified product 11 of Comparative Example 5.
FIG. 9 is an SEM image indicating a result of the blood compatibility test using a purified product 12 of Comparative Example 6.

DISCLOSURE OF THE INVENTION

Problem that the Invention is to Solve

An object of the present invention is to provide a surface treating agent excellent in antithrombogenicity, and accordingly, excellent in biocompatibility, and having high hydrophilicity as compared with conventional medical materials. Further, an object of the method for producing a (meth)acrylate copolymer of the present invention is to provide a production method excellent in performance of removing unreacted monomers and further improving a yield as compared with conventional production methods.

Means for Solving the Problem

The inventors of the present invention found that a copolymer obtained by copolymerizing (meth)acrylate having a hydrophilic polyethylene glycol backbone and hydrophobic long-chained alkyl(meth)acrylate maintains biocompatibility and blood compatibility of PEG, and at the same time is insoluble in water, and found out that coating a medical device with the copolymer can impart blood compatibility to the medical device. Further, the inventors found out that, since the obtained copolymer does not have a functional group with high polarity, such as an ionic group, activation of the immune system in the case of being in contact with blood can be suppressed. Furthermore, the present inventors found out that as a method for producing a (meth)acrylate copolymer maintaining blood compatibility and insoluble in water, unreacted monomers can be efficiently removed by using an aqueous solution obtained by mixing an alcohol and water at a specific ratio as a reprecipitation poor solvent and a copolymer can be obtained at a high yield, and the present invention was thus completed. That is, the present invention has the following structure.

The present invention provides a water-insoluble (meth)acrylate copolymer obtained by copolymerizing alkyl(meth)acrylate and methoxypolyethylene glycol(meth)acrylate.

It is preferable in the present invention that alkyl(meth)acrylate is expressed by the following general formula 1.

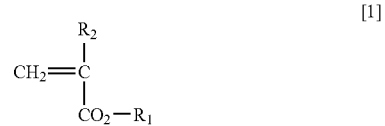

[1]

(In the formula, $R_1$ represents an alkyl group or aralkyl group having 2 to 30 carbon atoms, and $R_2$ represents a hydrogen atom or a methyl group.)

It is preferable in the present invention that methoxypolyethylene glycol(meth)acrylate is expressed by the following general formula 2.

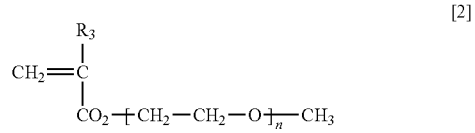

[2]

(In the formula, $R_3$ represents a hydrogen atom or a methyl group, and n represents an integer of 1 to 1,000.)

It is preferable in the present invention that the copolymer is obtained by copolymerizing alkyl(meth)acrylate and methoxypolyethylene glycol(meth)acrylate at a molar ratio of 30 to 90/10 to 70.

It is preferable in the present invention that the copolymer is soluble in any of alcohols having 1 to 6 carbon atoms.

It is preferable in the present invention that the copolymer has a glass transition temperature of –100 to 20° C.

It is preferable in the present invention that the copolymer has a number average molecular weight of 2,000 to 200,000.

Further, the present invention provides a method for producing a water-insoluble (meth)acrylate copolymer by copolymerizing hydrophobic (meth)acrylate and hydrophilic (meth)acrylate in a polymerization solvent that commonly dissolves hydrophobic (meth)acrylate and hydrophilic (meth) acrylate, and purifying the obtained copolymer to a purity of 90% by mol or more by reprecipitation.

It is preferable in the present invention that hydrophobic (meth)acrylate is alkyl(meth)acrylate.

It is preferable in the present invention that hydrophilic (meth)acrylate is methoxypolyethylene glycol(meth)acrylate.

It is preferable in the present invention that alkyl(meth)acrylate is expressed by the following general formula 1.

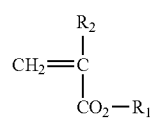

[1]

(In the formula, $R_1$ represents an alkyl group or aralkyl group having 2 to 30 carbon atoms, and $R_2$ represents a hydrogen atom or a methyl group.)

It is preferable in the present invention that methoxypolyethylene glycol(meth)acrylate is expressed by the following general formula 2.

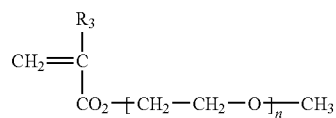

[2]

(In the formula, $R_3$ represents a hydrogen atom or a methyl group, and n represents an integer of 1 to 1,000.)

It is preferable in the present invention that the polymerization solvent and monomers are charged at a weight ratio of 20 to 90/80 to 10 and polymerization is performed.

It is preferable in the present invention that a (meth)acrylate copolymer is purified by using a mixed solution of an alcohol having 1 to 10 carbon atoms and water as a reprecipitation poor solvent.

It is preferable in the present invention that the reprecipitation poor solvent is obtained by mixing an alcohol having 1 to 10 carbon atoms and water at a weight ratio of 0.1 to 99.9:99.9 to 0.1.

It is preferable in the present invention that a (meth)acrylate copolymer solution and a reprecipitation poor solvent are mixed at a volume ratio of 1/5 to 1/10 and purification is performed when the copolymer is purified.

Furthermore, the present invention provides a medical device in which the (meth)acrylate copolymer is carried on at least a part of a surface thereof.

Advantages of the Invention

The copolymer of the present invention can be used as a material excellent in biocompatibility and having high hydrophilicity. Since the copolymer is a viscous substance insoluble in water, the copolymer can be coated to an entire portion being in contact with blood without damaging physical properties of a medical substrate. Further, since the method for producing a (meth)acrylate copolymer of the present invention can enhance the reactivity of a monomer as compared with a conventional production method, and can increase a removal rate of unreacted monomers in purification, exerted is an effect such that a surface-treating material excellent in antithrombogenicity and biocompatibility and having high hydrophilicity can be obtained at a high purity and a high yield.

BEST MODE FOR CARRYING OUT THE INVENTION

It is preferable in the present invention that the (meth) acrylate copolymer containing alkyl(meth)acrylate and methoxypolyethylene glycol(meth)acrylate is substantially water-insoluble. Herein, substantially water-insoluble indicates that when a (meth)acrylate copolymer is stood still with 99% by weight of physiological saline at 37° C. based on 1% by weight of the copolymer for 30 days, a weight loss of the copolymer is 1% by weight or less. Being water-insoluble is preferable from the viewpoint of preventing elusion of the copolymer into blood or the like even in the case of being in contact with tissues in a living body, blood, or the like.

It is preferable in the present invention that as alkyl(meth) acrylate of the following general formula 1, those in which $R_1$ has 2 to 30 carbon atoms, more preferably 4 to 24 carbon atoms, and further preferably 6 to 18 carbon atoms are used. Specific examples of such alkyl(meth)acrylate include normal hexyl(meth)acrylate, cyclohexyl(meth)acrylate, phenyl (meth)acrylate, heptyl(meth)acrylate, benzyl(meth)acrylate, octyl(meth)acrylate, 2-ethylhexyl(meth)acrylate, nonyl (meth)acrylate, decyl(meth)acrylate, lauryl(meth)acrylate, myristyl(meth)acrylate, palmityl(meth)acrylate, and stearyl (meth)acrylate. Among them, 2-ethylhexyl(meth)acrylate and lauryl(meth)acrylate are particularly preferable from the viewpoints of cost and performance.

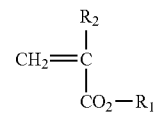

[1]

(In the formula, $R_1$ represents an alkyl group or aralkyl group having 2 to 30 carbon atoms, and $R_2$ represents a hydrogen atom or a methyl group.)

It is preferable in the present invention that as methoxypolyethylene glycol(meth)acrylate of the following general formula 2, those having 1 to 1,000 ethylene oxide units are used. More preferably those having 1 to 500, further preferably 1 to 100, still further preferably 2 to 50, and particularly preferably 2 to 10 ethylene oxide units are used. Specific examples thereof include methoxydiethylene glycol(meth) acrylate, methoxytriethylene glycol(meth)acrylate, methoxytetraethylene glycol(meth)acrylate, methoxypentaethylene glycol(meth)acrylate, methoxyhexaethylene glycol(meth) acrylate, methoxyheptaethylene glycol(meth)acrylate, methoxyoctaethylene glycol(meth)acrylate, methoxynonaethylene glycol(meth)acrylate, and methoxydecaethylene glycol (meth)acrylate. When a repeating unit is large and hydrophilicity is increased too much, even though copolymerization is performed, solubility into blood is high, and thus, there is a possibility of disappearing of copolymer from a medical material. Therefore, methoxytetraethylene glycol (meth)acrylate having 4 repeating ethylene oxide units and methoxytriethylene glycol(meth)acrylate having 3 repeating ethylene oxide units are preferable.

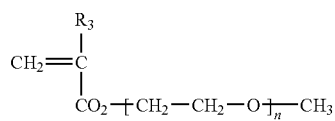

[2]

(In the formula, $R_3$ represents a hydrogen atom or a methyl group, and n represents an integer of 1 to 1,000.)

It is preferable in the present invention that a number average molecular weight of the (meth)acrylate copolymer is 2,000 or more from the viewpoint of easiness of purification by reprecipitation after polymerization. Further, as the molecular weight is larger, a viscosity becomes higher when a coating solution is prepared, and thus, there is a subsidiary effect such that adhesion with a substrate is improved. Therefore, the number average molecular weight of the (meth)acrylate copolymer is preferably 5,000 or more, and more preferably 7,000 or more. Further, setting the number average molecular weight to 200,000 or less is preferable from the viewpoint of decreasing the viscosity of a coating solution when the (meth)acrylate copolymer is applied to a material, and the like. More preferably the number average molecular weight is 100,000 or less, further preferably 50,000 or less, still further preferably 30,000 or less, and particularly preferably 18,000 or less. Herein, the number average molecular weight indicates a value obtained by dividing a sum of molecular weights of all molecules by a molecular number, which is one of the characteristics of a polymer.

Examples of a method of measuring a number average molecular weight include the end-group determination method, the osmotic pressure method, the vapor pressure osmometry, the vapor pressure depression method, the freezing point depression method, the ebullioscopy, and the gel permeation chromatography (GPC), and it is preferable in the present invention to employ the gel permeation chromatography (GPC) described later from the viewpoint of easiness of operation.

It is preferable in the present invention that alkyl(meth)acrylate and methoxypolyethylene glycol(meth)acrylate is copolymerized at a molar ratio of 30 to 90/10 to 70. When the amount of alkyl(meth)acrylate is too small, the copolymer is easily dissolved in blood or the like, and when the amount is too large, there is a possibility that blood compatibility of methoxypolyethyelene glycol(meth)acrylate cannot be sufficiently exerted. Therefore, the molar ratio is more preferably 40 to 90/10 to 60, further preferably 45 to 85/15 to 55, and still further preferably 50 to 80/20 to 50.

According to "Acrylic Resin, Synthesis/Design and Development of New Applications, Chubu Region Development Research Center, Inc., issued in 1985" and "Acrylic Ester and Its Polymer [II], Shokodo Co., Ltd., issued in 1975", as the number of carbon atoms in alkyl(meth)acrylate is increased, the glass transition temperature of the polymer is decreased, and after reaching a minimal value, the glass transition temperature tends to increase. The minimal value is 8 carbon atoms in n-alkyl acrylate, and 12 carbon atoms in n-alkyl methacrylate.

That is, it is indicated that by incorporating alkyl acrylate having 8 carbon atoms as a copolymerization component, the glass transition temperature of the copolymer can be lowered.

A methoxypolyethylene glycol(meth)acrylate homopolymer is excellent in blood compatibility since it has high hydrophilicity, but in the case of being brought into contact with blood or the like for a long period of time, since the copolymer is water-soluble, there has been a problem of gradual elusion. The inventors of the present invention made intensive studies on a material not only excellent in blood compatibility but also durable for a long term use, and as a result, they found that the problems can be solved by imparting suitable hydrophobicity for preventing elution into blood, or the like, and flexibility for preventing physical detachment of a coating. That is, they found out that a copolymer obtained by copolymerizing specific methoxypolyethylene glycol (meth)acrylate and specific alkyl(meth)acrylate as described above can solve the above described problems, and the present invention was thus completed.

It is preferable in the present invention that the (meth)acrylate copolymer is soluble in any of alcohols having 1 to 6 carbon atoms. It is more preferable that the (meth)acrylate copolymer is soluble in an alcohol having 1 to 3 carbon atoms because of easiness of drying after coating. Herein, being soluble indicates that at least 90% by weight of the (meth)acrylate copolymer dissolves within 48 hours at room temperature when 1 g of the (meth)acrylate copolymer is immersed in 10 mL of the above described alcohol at 25° C.

According to "Polymer Basic Science, Shokodo Co., Ltd., issued in 1991", when a polymer is cooled from a melting state, the polymer undergoes an excess cooled state without being crystallized and may be finally in a glass state to be solidified in some cases. The transformation from the melting state to the glass state is called glass transfer, and a temperature thereof is called a glass transition temperature. The polymer loses fluidity and is in a glass state at the glass transition temperature or lower, and on the other hand, at the glass transition temperature or higher, the polymer has fluidity and is, in a manner, in a liquid state. That is, to allow the copolymer of the present invention to have flexibility, it is required that the polymer has a glass transition temperature lower than room temperature (25° C.).

The glass transition temperature of the (meth)acrylate copolymer of the present invention is preferably −100 to 20° C. More preferably the glass transition temperature is −85 to 0° C., and further preferably −70 to −20° C. When the glass transition temperature is too high, there is a possibility that a copolymer coated to a substrate is physically detached from the substrate. When the glass transition temperature is too low, fluidity of the copolymer is increased to cause a possibility of lowering workability of coating.

The copolymer of the present invention may be any of a random copolymer, a block copolymer, and a graft copolymer. Further, a copolymerization reaction itself for producing the copolymer of the present invention is not particularly limited, and known methods such as radical polymerization, ion polymerization, photo polymerization, polymerization using a macromer, and the like can be used.

As one example for producing the (meth)acrylate copolymer of the present invention, a production method by radical polymerization will be described in the following.

That is, monomers, a polymerization solvent, and an initiator are added to a reaction apparatus equipped with a reflux condenser and capable of stirring, polymerization is initiated by heating the contents after replacement with nitrogen, and the polymerization is progressed by keeping the temperature for a specific time. It is preferable to perform bubbling of nitrogen during the polymerization. It is also possible to control a molecular weight by using a chain transfer agent in combination during this polymerization. The solvent is removed from the solution after the polymerization and a crude (meth)acrylate copolymer is obtained. Subsequently, the obtained crude (meth)acrylate copolymer is dissolved in a good solvent and dropped in a poor solvent under stirring to perform a purification treatment (hereinafter, may also be referred to as a reprecipitation treatment). The purity of the (meth)acrylate copolymer is increased by repeating the purification treatment once to several times. The copolymer thus obtained is dried.

As a polymerization solvent used in copolymerization, alcohols such as methanol, ethanol, and isopropyl alcohol, organic solvents such as ethyl acetate, toluene, benzene, and methyl ethyl ketone, or water can be used. Among them, ethyl acetate, methanol, ethanol and the like are preferably used in the present invention from the viewpoints of solubility of monomers and a copolymer to be obtained and availability thereof. Further, plural kinds of the above solvents can be used in the form of a mixture. A feed ratio of these polymerization solvent and monomers is preferably 20 to 90/80 to 10, more preferably 30 to 90/70 to 10, and further preferably 35 to 85/65 to 15. When the feed ratio is within this range, the polymerization reactivity can be enhanced to the maximum.

As a polymerization initiator, peroxide-based and azo-based radical initiators generally used in radical polymerization are used. Examples of the peroxide-based radical initiators include inorganic peroxides such as potassium persulfate, ammonium persulfate, and hydrogen peroxide, and organic peroxides such as benzoyl peroxide, t-butyl hydroperoxide, and cumene peroxide, and examples of azo-based radical initiators include 2,2'-azobisisobutylonitrile, 2,2'-azobis(2-amidinopropane) dihydrochloride, dimethyl 2,2'-azobisbutylate, and dimethyl 2,2'-azobis(2-methylpropyonate). Further, a redox initiator obtained by combining a reducing agent with a peroxide-based polymerization initiator can be also used. These polymerization initiators are preferably added in an amount of 0.01 to 1% by weight based on monomers in a polymerization solution. More preferable amount to be added is 0.05 to 0.5% by weight, and 0.05 to 0.3% by weight is further preferable. Setting an amount to be added of the polymerization initiator, or the like within such a range enables to obtain a copolymer having a suitable number average molecular weight by a good monomer reactivity.

A temperature in polymerization differs depending on a kind of a solvent and a kind of an initiator, but it is preferable to employ a temperature around a temperature of a 10-hour half life period of an initiator. Specifically, 20 to 90° C. is preferable when the above described initiators are used. 30 to 90° C. is more preferable, and 40 to 90° C. is further preferable. As a chain transfer agent used for controlling a molecular weight in polymerization, thiol compounds having a high boiling point such as dodecyl mercaptan, thiomalic acid and thioglycolic acid, isopropyl alcohol, phosphorous acid, hypophosphorous acid, and the like can be used.

As a specific example of a method of a reprecipitation treatment, for example, it is preferable that a (meth)acrylate copolymer is dissolved in a good solvent, and the (meth)acrylate copolymer solution is dropped in a reprecipitation solvent during stirring, thereby purifying the copolymer. In this method, the reprecipitation poor solvent has a volume preferably 5 to 10 times that of the solution of the crude (meth)acrylate copolymer solution. By setting the volume in this range, the (meth)acrylate copolymer can be efficiently recovered. When the copolymer cannot be sufficiently purified with one reprecipitation, two or more times of the same operations may be performed.

Since the (meth)acrylate copolymer is made by copolymerizing a hydrophilic monomer and a hydrophobic monomer in the present invention, the (meth)acrylate copolymer has an intermediate property between hydrophilicity and hydrophobicity. Therefore, a hydrophilic monomer (methoxypolyethylene glycol(meth)acrylate) and a hydrophobic monomer (alkyl(meth)acrylate), which are unreacted monomers, and a (meth)acrylate copolymer are present in a solution after copolymerization. In order to isolate a water-insoluble (meth)acrylate copolymer from the mixture of these components, for example, the copolymer solution is dropped in a reprecipitation liquid dissolving the hydrophilic monomer to perform purification, and subsequently, the copolymer is purified by using a reprecipitation liquid dissolving the hydrophobic monomer. However, in such a combination of purification methods, there are problems that not only a purification operation is complicated, but also a purification cost increases and loss of the copolymer is large. The inventors of the present invention made intensive studies on a purification method for obtaining a (meth)acrylate copolymer with a simple and easy purification operation, and at low cost and a high yield; as a result, they found out that the (meth)acrylate copolymer can be efficiently recovered by using a reprecipitation poor solvent obtained by mixing an alcohol and water at a specific ratio.

As a solvent used for purifying the copolymer by reprecipitation, a solvent that does not dissolve the copolymer but dissolves both of the hydrophilic monomer and the hydrophobic monomer is preferably used in the present invention. In order to precipitate the (meth)acrylate copolymer, when only an alcohol is used, it is required to improve or decrease hydrophilicity of the alcohol. Examples of a method of controlling hydrophilicity of the alcohol include a method of using an alcohol by mixing a solvent having high hydrophilicity. Specific examples of such a solvent include water, 1,4-dioxane, tetrahydrofuran, N-methylpyrrolidone, N,N-dimethylformamide, and N,N-dimethylacetamide, and it is preferable to use water from the viewpoints of easiness of volatilization and cost. By using an alcohol and water in the form of a mixture at a specific mixing ratio as a poor solvent, hydrophilicity can be controlled and the (meth)acrylate copolymer can be obtained at a high yield.

It is preferable to use an alcohol having 1 to 10 carbon atoms, more preferably 1 to 7 carbon atoms, and further preferably 1 to 4 carbon atoms as an alcohol used for a reprecipitation liquid in the present invention. Specific examples of such an alcohol include methanol, ethanol, 1-propanol, 2-propanol, 1-butanol, 2-butanol, 2-methoxy-1-propanol, and tertiary butanol. Among them, methanol and ethanol are particularly preferable form the viewpoint that short time drying at low temperature is possible.

It is preferable to use an alcohol having 1 to 10 carbon atoms and water in the form of a mixture at a weight ratio of 0.1 to 99.9/99.9 to 0.1, more preferably 30 to 99/70 to 1, and further preferably 50 to 95/50 to 5 in the present invention. When a ratio of an alcohol is too large, the (meth)acrylate copolymer is hardly precipitated, and when a ratio of water is too large, there is a possibility that unreacted monomers are mixed in the precipitated (meth)acrylate copolymer as an impurity, and thus, the weight ratio is particularly preferably 70 to 95/30 to 5.

It is preferable in the present invention that a mixed solution of an alcohol having 1 to 10 carbon atoms and water is used as a poor solvent for reprecipitation. A good solvent may be a solvent dissolving the (meth)acrylate copolymer and miscible with the poor solvent. Specific examples thereof include tetrahydrofuran, chloroform, acetone, ethyl acetate, N,N-dimethylformamide, N,N-dimethylacetamide, and N-methylpyrrolidone. Among them, tetrahydrofuran and acetone having a low boiling point are particularly preferable from the viewpoint of being easily dried. It is preferable to purify the copolymer by repeating reprecipitation in which these substances are used as a good solvent and added to the above poor solvent plural times.

Performing the reprecipitation operation as described above 2 to 5 times as necessary makes it possible to recover a water-insoluble (meth)acrylate copolymer containing less than 1% by mol of unreacted monomers at such a high yield as 50% by weight or more.

When the yield of the (meth)acrylate copolymer after reprecipitation exceeds 90% by weight in the present invention, there causes a possibility that the unreacted monomers are remained at a high concentration in the recovered product, and thus, the yield is preferably 50 to 90% by weight.

In order to use a purified copolymer as a coating material, it is necessary to remove a solvent by drying. As a drying method, for example, drying is carried out at 60° C. under a reduced pressure of 1 Torr or less continuously for 2 to 10 days, and when sufficient dryness cannot be obtained, drying with reduced pressure may be successively performed. The purity of the thus obtained (meth)acrylate copolymer is preferably 90% by mol or more. When the purity of the copolymer is 90% by mol or more, for example, in the case of using the copolymer as a coating material of medical devices as described later, materials having high safety for a medical application, such as no elution of a monomer, an oligomer, or the like into the blood, can be provided.

In the present invention, since the (meth)acrylate copolymer obtained by copolymerizing alkyl(meth)acrylate and methoxypolyethylene glycol(meth)acrylate has appropriate balance of hydrophilicity and hydrophobicity, biocompatibility and furthermore, antithrombogenicity are excellent, and thus, the (meth)acrylate copolymer can be preferably used for surface-treatments of medical devices and artificial organ membranes. The copolymer can be used alone and two or more kinds thereof can be also used in the form of a mixture.

A medical device on which the copolymer of the present invention is carried can be obtained, for example, by applying a solution obtained by dissolving the copolymer in an organic solvent on a surface of a substrate of the medical device or the like, and thereafter removing the solvent. As a method of carrying the copolymer of the present invention on a surface of the substrate of a medical device or the like, known methods such as a coating method, methods using graft polymerization by radiation, electron beams, and ultraviolet rays, and a method using a chemical reaction with a functional group of a substrate can be mentioned. Among these methods, the coating method is practically preferable since a treatment is simple and easy. The coating method is not particularly limited, and an application method, a spray method, a dip method, and the like can be used. For example, a coating method by the application method can be carried out by an easy operation such as immersion of a substrate in a coating liquid obtained by dissolving the (meth)acrylate copolymer of the present invention in a suitable organic solvent (e.g., alcohol, chloroform, acetone, tetrahydrofuran, or dimethylformamide), removal of an excess solution, and subsequent air drying. Further, it is also preferable to dry by heating the substrate after coating. Thus, adhesion between the substrate and the copolymer of the present invention can be more increased and the copolymer can be more firmly carried on the substrate.

As an organic solvent for applying the copolymer of the present invention to a substrate, solvents giving as less damage as possible to a medical device that is a substrate are selected, and specific examples thereof include methanol, ethanol, isopropyl alcohol, normal propyl alcohol, acetone, normal hexane, cyclohexane, tetrahydrofuran, 1,4-dioxane, cyclohexanone, N,N-dimethylformamide, N,N-dimethylacetamide, and N-methylpyrrolidone, and among these, methanol, ethanol and isopropyl alcohol having a low boiling point and easily dried after coating are more preferable.

The medical device of the present invention is preferably treated with the (meth)acrylate copolymer of the present invention at least in a part on its surface, preferably in the entire part being in contact with blood or the like on its surface. Particularly, it is one of preferable embodiments that the copolymer of the present invention is carried on a medical device, or the like, which is required to have excellent antithrombogenicity. Examples of such a medical device include a blood filter, a blood preservation container, a blood circuit, an indwelling needle, a catheter, a guide wire, a stent, an artificial lung device, a dialyzer, an adhesion preventing material, a wound dressing material, an adhesive material for tissues in a living body, and a repairing material for living tissue reproduction. In particular, preferable is a medical device having an extracorporeal circulation circuit in which a blood contact part is present.

Herein, materials for the medical device include all materials generally used. That is, examples thereof include vinyl polychloride, polycarbonate, polyethylene terephthalate, polyethylene, polypropylene, polymethyl pentene, thermoplastic polyether polyurethane, thermosetting polyurethane, silicone rubbers such as polydimethylsiloxane having a crosslinking part, polymethyl methacrylate, polyvinylidene fluoride, polyethylene tetrafluoride, polysulfone, polyethersulfone, polyacetal, polystyrene, ABS resins and mixtures of these resins, and metals such as stainless steel, titanium, and aluminum.

In the present invention, when a medical device subjected to a treatment using the (meth)acrylate copolymer is in contact with blood, it is considered that methoxypolyethylene glycol(meth)acrylate having high hydrophilicity extends to a surface and exerts antithrombogenicity, and further, alkyl (meth)acrylate remains around the substrate to prevent blood and the medical device from being directly in contact with each other.

In the present invention, a method of confirming water insolubility of the (meth)acrylate copolymer may be an aging treatment. It is preferable to use physiological saline as an extraction solvent used in the aging treatment from the viewpoints of improving simplicity and reliability of the blood compatibility evaluation that is carried out later. The aging treatment is further preferably carried out at a constant temperature of 37° C. When the (meth)acrylate copolymer is water-insoluble, high blood compatibility is maintained after the aging treatment.

In the present invention, examples of a method of evaluating a degree of immunity activation of the (meth)acrylate copolymer include comparison of complement values. The Mayer method of measuring CH50 makes it possible to perform a simple and rapid measurement, and furthermore, the method is preferable since a measuring kit is easily available and inexpensive (see Jinkou Zouki 23(3), p. 654-659 (1994)). By reacting the sensitized sheep erythrocytes and a complement in serum, the sensitized erythrocytes are hemolyzed. Since a hemolytic degree is lowered as the complement system is activated, the method can be advantageously used for evaluation.

As another method of the immune system evaluation of the present invention, an assay of C3a called anaphylatoxin can be mentioned. When C3a is produced in a living body, change of blood vessel permeability, contraction of smooth muscle, and histamine release by obesity cells and basophil granulocytes are caused and an inflammatory reaction is mainly generated (see The Molecular Biology of a Complement—the role in the biophylaxis—, Nankodo Co., Ltd). A larger numerical value of C3a means that the complement system is more activated, and by comparison of the numerical values, the method can be advantageously utilized as an evaluation method.

As one method of blood compatibility evaluation of (meth) acrylate in the present invention, a fibrin gel forming experiment can be mentioned. By this technique, an activation degree of fibrinogen that is one of blood coagulation factors can be evaluated. Specifically, a reaction of gelling of fibrinogen in plasma by calcium ions to form a fibrin gel is utilized. The technique is preferable since activation of the blood coagulation system can be easily evaluated without requiring a specific measuring apparatus by measuring a time required for gelation in the calcium ion-added plasma being in contact with a sample (hereinafter referred to as a gelation time). A longer gelation time means that an action of foreign matter recognition in blood proteins is hardly caused, which indicates high blood compatibility.

EXAMPLES

The present invention will now be further specifically illustrated by using the following Examples although the present invention is not limited thereto.

(Measurement of Number Average Molecular Weight)

3 mL of a transfer phase for GPC measurement was added to 15 mg of a sample, then the sample was dissolved and filtration was performed with 0.45 μm of a hydrophilic PTFE (Millex-LH, made by Millipore Japan Co.). Measuring apparatuses of a 510 high pressure pump, a 717 plus automatic injection device (made by Nihon Waters K.K.), and RI-101 (made by Showa Denko K.K.) were used for the GPC measurement, and PLgel 5μ MIXED-D (600×7.5 mm) (made by Polymer Laboratories, Ltd.) was used for a column, and the measurement was performed at a normal column temperature, and tetrahydrofuran (THF) added with 0.03% by weight of dibutyl hydroxy toluene (BHT) was used as the transfer phase. Detection was performed at RI, and 50 μL, of the test sample solution was injected. Molecular weight composition was performed by single dispersion PMMA (Easi Cal: made by Polymer Laboratories, Ltd.).

(Measurement of a Copolymerization Composition Ratio)

50 mg of the sample was added to an NMR test tube (speculation: N-5, made by Nihon Seimitsu Kagaku Co., Ltd.) with a Pasteur pipette, and then, 0.7 mL of chloroform-d (made by Wako Pure Chemical Industries, Ltd.) was added thereto to be sufficiently blended, and the test tube was covered with a cap for the sample (speculation: NC-5, made by Nihon Seimitsu Kagaku Co., Ltd.). A copolymerization composition ratio was calculated by carrying out 1H NMR measurement under room temperature using GEMINI-200 made by VARIAN Co.

(Alcohol-Solubility Test)

500 mg of the sample was added to a 50 mL-vial, and 2 mL of an alcohol having any of 1 to 6 carbon atoms was then added to be sufficiently blended. Then, dissolution was visually confirmed.

(Measurement of a Glass Transition Temperature)

A differential scanning calorimeter (DSC-50, made by SHIMADZU CORPORATION) was used. 10 mg of the sample was packed in a cell (Al cell, 6 mmφ, made by SHIMADZU CORPORATION) and covered with a lid, and crimped and sealed with a sealer crimper (made by SHIMADZU CORPORATION), and then, the sample was set in a measuring apparatus to be measured. The measurement was carried out from −150° C. to 60° C. at a heating rate of 5° C./rain under an $N_2$ gas air flow after cooling with liquid nitrogen.

(Aging Treatment)

19.8 g of ethanol (tetrahydrofuran was used only in Comparative Example 6) was added to 0.2 g of the sample and then the sample was dissolved, thereby preparing 1% by weight of an ethanol (tetrahydrofuran was used only in Comparative Example 6) solution to obtain a surface treating agent. The surface treating agent was applied to a vinyl chloride sheet with a size of 25×25×1 mm, and the sheet was dried at 60° C. for 24 hours. Further, aging was performed for 30 days in physiological saline at 37° C. to form an aging sample for a blood compatibility test. Regarding the samples after 30 days-aging, samples having a weight reduction rate of 20% by weight or less were evaluated as good, and samples having a weight reduction rate of more than 20% by weight were evaluated as poor. It can be determined that the samples were significantly dissolved in physiological saline in the case of 20% or more of weight reduction even considering an error of measurement.

(Blood Compatibility Test)

60 mL of citrated fresh blood removed from a rabbit was equally divided in two 50 mL-centrifuge tubes, and centrifuged at 1000 rpm for 10 minutes. The supernatants thereof were equally divided in four 10 mL-centrifuge tubes. The supernatants were further centrifuged at 1500 rpm for 10 minutes, and the supernatants were then removed to separate platelet pellets that were a precipitate. Thereto was added HBSS (Hanks' balanced salt solution) for dilution to thereby obtain a platelet solution having a platelet concentration of $3.0 \times 10^8$/mL. The platelet concentration was confirmed with a blood cell counter (KX-21, made by SYSMEX CORPORATION). The platelet solution having this concentration was used as a test solution. 0.2 mL of the obtained test solution was taken and dropped on the upper surface of an aging sample for a blood compatibility test in a 60×15 mm petri dish (made of polystyrene, made by Corning Inc.), thereafter covered with a lid and incubated at 37° C. for 1 hour. Then, 5 mL of an aqueous solution containing 2.5% by weight of glutaric aldehyde was added thereto and the mixture was stood still at room temperature for 24 hours. An operation of replacing the solution in the petri dish with water was performed three times, and water was then removed. A vinyl chloride sheet washed with water was frozen at −5° C. for 24 hours, and then dried at 0.1 Torr for 24 hours. A piece with a size of 10×10 mm was cut out from a portion attached with platelets, and adhered to a sample table for a scanning electron microscope (SEM) with a double sided tape to be used as a measurement sample. Conditions of adhered platelets were photographed by SEM using the sample having been subjected to ion vapor deposition. The SEM photos (×3000 times) taken were visually observed for comparison, and the case where the attached platelet number was 50 or less was evaluated to be good.

(Complement Evaluation—Sample Preparation)

A solution obtained by adding 19.8 g of ethanol (tetrahydrofuran was used only in Comparative Example 6) to 0.2 g of the sample and dissolving the sample was used as a surface treating agent, and brought in contract with 1 g of a glass ball with a diameter of 1 mm to remove the solution, and then dried at 60° C. for 24 hours to thereby prepare a sample. Further, the sample was subjected to aging in physiological saline at 37° C. for 30 days, washed with distilled water, and then dried at 60° C. for 8 hours to be a sample for complement (complement value and C3a) evaluation.

(Measurement of Complement—Complement value)

10 mL of human fresh blood separated in a 50 mL-centrifuge tube made of polypropylene (made by IWAKI Co., Ltd.) was coagulated by standing still at room temperature and centrifuged at 3000 rpm for 30 minutes (LC06, made by TOMY SEIKO Co., Ltd.) to thereby obtain 3.5 mL of serum. 0.1 mL of a diluted liquid was added to 1 g of 1 mmϕ glass beads with subjected to a surface-treatment by the above described method, and then incubated at 37° C. for 1 hour, and 0.2 mL of the obtained serum added thereto and incubated at 37° C. for 1 hour in the same manner. 2.6 mL of the diluted liquid, 12.5 μL, of serum in contact, and 0.4 mL of sensitized sheep erythrocytes were sufficiently mixed, and then incubated at 37° C. for 1 hour, cooled at 0° C. for 10 minutes, and then centrifuged at 2000 rpm, and an absorbance of 2 mL of the supernatant was measured at 541 nm (U-2000 Spectrometer, made by HITACHI, Ltd.). At the same time, a mixture of 2.6 mL of a diluted liquid and 0.4 mL of sensitized sheep erythrocytes was considered as a solution without hemolysis and data thereof was deducted. Auto CH50-L "Seiken" (universal product No. 400437, 52 mL of diluted liquid, 6 mL of sensitized sheep erythrocytes) was used for measurement. A relative absorbance was calculated based on an absorbance of a glass ball that is not subjected to a surface-treatment as 1, and 1.2 or more was evaluated to be good, and less than 1.2 was evaluated to be defective. In the case of less than 1.2, it can be determined that a complement was significantly activated even considering a measurement error.

(Measurement of Complement—C3a)

10 mL of human fresh blood separated in a 50 mL-centrifuge tube made of polypropylene (made by IWAKI Co., Ltd.) and 1 mL of an aqueous solution containing 3.2% by weight of trisodium citrate were sufficiently mixed, and then centrifuged at 2000 rpm for 30 minutes (LC06, made by TOMY SEIKO Co., Ltd.) to thereby obtain 4.5 mL of plasma. 0.5 mL of physiological saline was added to 4.6 g of 1 mmϕ glass beads that had been subjected to a surface-treatment by the above described method, and then incubated at 37° C. for 1 hour, thereto was added 1 mL of the obtained plasma, incubation was performed at 37° C. for 1 hour in the same manner, and 0.5 mL of the solution was used as an evaluation sample. The sample was rapidly cooled to −20° C. or lower and stored until measurement.

The evaluation was performed by using Human Complement C3a Des Arg[$^{125}$I] Biotrak Assay System, code RPA518 (made by Amersham Biosciences, Corp.) according to an attached manual.

The evaluation value was calculated as an average value of the three data, and since a value of an untreated evaluation sample was 94 ng/mL, it was considered that when the C3a value was 100 ng/mL or more, the complement was significantly activated even considering a measurement error, and thus, the value was evaluated to be defective, and the case of less than 100 ng/mL was evaluated to be good.

(Fibrin Gel Formation Experiment)

45 mL of citrated bovine blood in a 50 mL-centrifuge tube made of polypropylene (made by IWAKI Co., Ltd.) was centrifuged at 2000 rpm for 30 minutes (LC06, made by TOMY SEIKO Co., Ltd.) to thereby obtain 8 mL of bovine blood plasma. 1 g of 1 mmϕ) glass beads subjected to a surface-treatment by the above described method and the centrifuge tube made of polystyrene that had been surface-treated in the interior surface in the same manner were used as evaluation samples. 1.8 mL of bovine plasma was added to the centrifuge tube in which glass beads after the surface-treatment are sealed, and then incubated at 37° C. for 3 minutes, 0.2 mL of an aqueous solution with 0.125 N of $CaCl_2$ was added thereto and mixed, and the time immediately after the mixing was considered to be reaction initiation and the mixture was incubated at 37° C. Presence or absence of completion of gelation was confirmed at an interval of 10 seconds after the reaction initiation, and a gelation time was measured. The N number was assumed to be 5, and an average value thereof was calculated. Since a coagulation time of a surface-untreated sample was 635 seconds, the coagulation system was significantly activated in the case of less than 600 seconds even considering a measurement error, and thus, the value was evaluated to be defective, and the case of 600 seconds or more was evaluated to be good. Further, a protein concentration in the bovine blood plasma used in the experiment was calculated by a weighing amount after freeze drying and found to be 82 mg/mL.

(Calculation of a Yield)

A copolymer weight ratio after reprecipitation and drying against a total amount of charged monomers was calculated as a yield (%).

(Measurement of Remaining Amount of Unreacted Monomers)

50 mg of the sample was added to an NMR test tube (speculation: N-5, made by Nihon Seimitsu Kagaku Co., Ltd.) with a Pasteur pipette, and then, 0.7 mL of chloroform-d (made by Wako Pure Chemical Industries, Ltd.) was added thereto to be sufficiently blended, and the test tube was covered with a cap for the sample (speculation: NC-5, made by Nihon Seimitsu Kagaku Co., Ltd.). A copolymerization composition ratio was calculated by carrying out 1H NMR measurement under room temperature using GEMINI-200 made by VARIAN Co. The amount of the unreacted monomers contained in the (meth)acrylate copolymer was calculated from the integral ratio obtained by the measurement, and the unreacted monomer content of less than 1% by mol was evaluated to be good, and the content of 1% by mol or more was evaluated to be defective. When no precipitate was observed by reprecipitation, it was evaluated to be disapproved.

Example 1

To a reaction apparatus equipped with a reflux condenser and capable of stirring, 15.1 g of methoxytriethylene glycol acrylate (MTEGA) (made by SHIN-NAKAMURA CHEMICAL CO., LTD.), 29.7 g of 2-ethylhexyl acrylate (EHA) (made by TOKYO CHEMICAL INDUSTRY CO., LTD.), 0.0447 g of azobisisobutyronitrile (AIBN) (made by Wako Pure Chemical Industries, Ltd.), and 178.9 g of ethanol (made by TOKYO CHEMICAL INDUSTRY CO., LTD.) were added, and a polymerization reaction was performed at 80° C. for 20 hours. The inside of the reaction apparatus was replaced with nitrogen in advance, and further, nitrogen bubbling was continued during the polymerization reaction. After completion of the polymerization reaction, a polymerization solvent was removed by evaporation for 4 days under the conditions of 60° C. and 1 Torr, and a crude (meth)acrylate copolymer was obtained. 2 g of the obtained crude (meth) acrylate copolymer was dissolved in 2 g of tetrahydrofuran and dropped in 20 g of a poor solvent (weight ratio of methanol/water was set to 80/20) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 1.

Example 2

The same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 85/15) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 2.

Example 3

The same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 90/10) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 3.

Example 4

To a reaction apparatus equipped with a reflux condenser and capable of stirring, 22.2 g of MTEGA (made by SHIN-NAKAMURA CHEMICAL CO., LTD.), 33.8 g of EHA (made by TOKYO CHEMICAL INDUSTRY CO., LTD.), 0.0543 g of azobisisobutyronitrile (AIBN) (made by Wako Pure Chemical Industries, Ltd.), and 84.2 g of ethanol (made by TOKYO CHEMICAL INDUSTRY CO., LTD.) were added, and a polymerization reaction was performed at 80° C. for 20 hours. After completion of the polymerization reaction, the same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 80/20) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 4.

Example 5

To a reaction apparatus equipped with a reflux condenser and capable of stirring, 33.4 g of methoxytriethylene glycol acrylate (MTEGA) (made by SHIN-NAKAMURA CHEMICAL CO., LTD.), 38.9 g of lauryl acrylate (LA) (made by TOKYO CHEMICAL INDUSTRY CO., LTD.), 0.0747 g of azobisisobutyronitrile (AIBN) (made by Wako Pure Chemical Industries, Ltd.), and 48.2 g of ethanol (made by TOKYO CHEMICAL INDUSTRY CO., LTD.) were added, and a polymerization reaction was performed at 80° C. for 20 hours. After completion of the polymerization reaction, the same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 95/5) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 5.

Example 6

To a reaction apparatus equipped with a reflux condenser and capable of stirring, 22.2 g of methoxytriethylene glycol acrylate (MTEGA) (made by SHIN-NAKAMURA CHEMICAL CO., LTD.), 44.2 g of lauryl acrylate (LA) (made by SHIN-NAKAMURA CHEMICAL CO., LTD.), 0.0655 g of azobisisobutyronitrile (AIBN) (made by Wako Pure Chemical Industries, Ltd.), and 66.4 g of ethanol (made by TOKYO CHEMICAL INDUSTRY CO., LTD.) were added, and a polymerization reaction was performed at 80° C. for 20 hours. After completion of the polymerization reaction, the same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 95/5) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 6.

Comparative Example 1

The same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 100/0) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 7.

Comparative Example 2

The same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 0/100) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 8.

Comparative Example 3

To a reaction apparatus equipped with a reflux condenser and capable of stirring, 95.2 g of methoxypolyethylene glycol (MW=400) acrylate (MPEGA) (made by SHIN-NAKAMURA CHEMICAL CO., LTD.), 5.1 g of ethyl acrylate (EA) (made by TOKYO CHEMICAL INDUSTRY CO., LTD.), 0.125 g of azobisisobutyronitrile (AIBN) (made by Wako Pure Chemical Industries, Ltd.), and 250 g of isopropyl alcohol (made by TOKYO CHEMICAL INDUSTRY CO., LTD.) were added, and a polymerization reaction was performed at 80° C. for 20 hours. After completion of the polymerization reaction, the same operation as in Example 1 was carried out, and a crude (meth)acrylate copolymer was obtained. 2 g of the obtained crude (meth)acrylate copolymer was dissolved in 2 g of tetrahydrofuran and dropped in 20 g of a poor solvent (weight ratio of methanol/water was set to 80/20) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 9.

Comparative Example 4

To a reaction apparatus equipped with a reflux condenser and capable of stirring, 22.3 g of 2-ethylhexyl acrylate (EHA) (made by TOKYO CHEMICAL INDUSTRY CO., LTD.), 0.0467 g of azobisisobutyronitrile (AIBN) (made by Wako Pure Chemical Industries, Ltd.), and 100 g of ethyl acetate (made by TOKYO CHEMICAL INDUSTRY CO., LTD.) were added, and a polymerization reaction was performed at 80° C. for 20 hours. 2 g of the obtained crude (meth)acrylate copolymer was dissolved in 2 g of tetrahydrofuran and dropped in 20 g of a poor solvent (weight ratio of methanol/water was set to 80/20) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 10.

Comparative Example 5

In a reaction apparatus equipped with a reflux condenser and capable of stirring, 10.0 g of 2-methacryloyloxy oxyethyl phosphorylcholine (MPC), 10.0 g of butyl methacrylate (BMA), and 0.069 g of t-butylperoxy neodecanoate were dissolved in an aqueous mixed medium consisting of 30% by weight of water and 70% by weight of ethanol to be a total amount of 100 g (20% by weight of a monomer concentration in the entire polymerization solvent). This solution was immersed in a hot bath at 50° C. and polymerized for 6 hours. After completion of the polymerization reaction, the reaction solution was dropped into n-hexane for precipitation, and a generated product was isolated. The operation of dissolving the generated product in ethanol, and dropping the product into n-hexane was performed twice to purify the product. This product was dried at reduced pressure for 4 days under the condition of a reduced pressure at 0.1 Torr at 60° C. to thereby obtain a purified product 11.

Comparative Example 6

To a reaction apparatus equipped with a reflux condenser and capable of stirring, 25.6 g of 2-methoxyethyl acrylate (MEA) (made by TOKYO CHEMICAL INDUSTRY CO., LTD.), 0.0246 g of azobisisobutyronitrile (AIBN) (made by Wako Pure Chemical Industries, Ltd.), and 119.1 g of dimethylacetamide (made by Kishida Chemical CO., LTD.) were added, and a polymerization reaction was performed at 80° C. for 20 hours. The obtained polymer solution was dropped in n-hexane under stirring using a Pasteur pipette, and a crude polymer was obtained. 2 g of the obtained crude polymer was dissolved in 2 g of tetrahydrofuran and dropped in 20 g of a poor solvent (n-hexane) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a purified product 12.

TABLE 1

|  | Example 1 | Example 2 | Example 3 | Example 4 | Example 5 | Example 6 |
|---|---|---|---|---|---|---|
| Hydrophobic (meth)acrylate | EHA | ← | ← | ← | LA | ← |
| Number of carbon atoms in $R_1$ | 8 | ← | ← | ← | 12 | ← |
| Hydrophilic (meth)acrylate | MTEGA | ← | ← | ← | ← | ← |
| N number | 3 | ← | ← | ← | ← | ← |
| Ratio of hydrophobic (meth)acrylate/hydrophilic (meth)acrylate | 73.5/26.5 | 71.2/28.8 | 69.5/30.5 | 66.8/33.2 | 56.4/43.6 | 70.6/29.4 |
| Solubility to alcohols having 1 to 6 carbon atoms | ○ | ○ | ○ | ○ | ○ | ○ |
| Water-insolubility | ○ | ○ | ○ | ○ | ○ | ○ |
| Glass transition temperature (° C.) | −58 | −58 | −58 | −65 | −40 | −31 |
| Aging treatment | ○ | ○ | ○ | ○ | ○ | ○ |
| Blood compatibility test | good | good | good | good | good | good |
| Number average molecular weight of the (meth)acrylate copolymer | 12,000 | 1,2000 | 12,000 | 15,000 | 9,000 | 8,000 |
| Complement value | 1.21 | 1.29 | 1.38 | 1.44 | 1.22 | 1.31 |
| Determination | good | good | good | good | good | good |
| C3a | 90 | 92 | 87 | 83 | 89 | 95 |
| Determination | good | good | good | good | good | good |
| Fibrin formation experiment | 780 | 800 | 850 | 830 | 730 | 710 |
| Determination | good | good | good | good | good | good |
| Ratio of methanol/water | 80/20 | 85/15 | 90/10 | 80/20 | 95/5 | 95/5 |
| Yield (%) | 72 | 68 | 53 | 58 | 84 | 87 |
| Determination | good | good | good | good | good | good |
| Remaining amount of unreacted monomers (mol %) | 0 | 0 | 0 | 0 | 0 | 0 |
| Determination | good | good | good | good | good | good |

TABLE 2

| | Comparative Example 1 | Comparative Example 2 | Comparative Example 3 | Comparative Example 4 | Comparative Example 5 | Comparative Example 6 |
|---|---|---|---|---|---|---|
| Hydrophobic (meth)acrylate | EHA | EHA | EA | EHA | BMA | — |
| Number of carbon atoms in $R_1$ | 8 | ← | 2 | 8 | 4 | — |
| Hydrophilic (meth)acrylate | MTEGA | ← | MPEGA | — | MPC | MEA |
| N number | 3 | ← | 9 | — | — | — |
| Ratio of hydrophobic (meth)acrylate/hydrophilic (meth)acrylate | — | 71.2/28.8 | 15.7/84.3 | 100/0 | — | — |
| Solubility to alcohols having 1 to 6 carbon atoms | — | ○ | ○ | ○ | ○ | ○ |
| Water-insolubility | — | ○ | water-soluble | ○ | ○ | ○ |
| Glass transition temperature (° C.) | — | −59 | −70 | −57 | — | −36 |
| Aging treatment | — | ○ | x | ○ | ○ | ○ |
| Blood compatibility test | — | defective | defective | defective | defective | good |
| Number average molecular weight of the (meth)acrylate copolymer | — | 11,000 | — | 20,000 | — | 11,000 |
| Complement value | — | — | — | 1.32 | 1.05 | 0.94 |
| Determination | — | — | — | good | defective | defective |
| C3a | — | — | — | 98 | 169 | 114 |
| Determination | — | — | — | good | defective | defective |
| Fibrin formation experiment | — | — | — | 620 | 935 | 425 |
| Determination | — | — | — | good | good | defective |
| Ratio of methanol/water | 100/0 | 0/100 | 80/20 | 80/20 | — | — |
| Yield (%) | 0 | 95 | 0 | 96 | — | — |
| Determination | defective | defective | defective | defective | — | — |
| Remaining amount of unreacted monomers (mol %) | — | 6 | — | 8 | — | — |
| Determination | disapproved | defective | disapproved | defective | — | — |

As shown in Tables 1 and 2, as a result of the blood compatibility test and the complement evaluation, it was found that the number of adhered platelets on a surface was small and good blood compatibility was shown in examples. In addition, as a result of the immune system evaluation, it was found that the copolymer of the present invention has good complement activity suppression effects.

In the present invention, it was found that good blood compatibility was shown even after aging for 30 days. Accordingly, maintenance of performance for a long time is expected. Further, it was found that removal of unreacted monomers and securement of a yield were possible. Thus, application of the copolymer to medical devices will be facilitated.

INDUSTRIAL APPLICABILITY

The copolymer of the present invention can be used as a material excellent in blood compatibility and having high hydrophilicity. Since the physical property of the copolymer as a material is a viscous substance insoluble in water, the present invention can provide a material which can be coated to an entire portion of a blood circuit without damaging physical properties of a medical device. Further, the present invention can provide a production method excellent in blood compatibility and in performance of removing unreacted monomers and further improving a yield as compared with a conventional production method. Therefore, the present invention highly contributes in an industrial growth.

The invention claimed is:

1. A water-insoluble (meth)acrylate copolymer obtained by copolymerizing alkyl(meth)acrylate and methoxypolyethylene glycol (meth)acrylate, wherein
the alkyl (meth)acrylate is a compound of formula [1]:

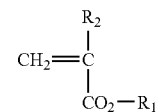

[1]

wherein $R_1$ represents an alkyl group or aralkyl group having 6 to 18 carbon atoms, and $R_2$ represents a hydrogen atom or a methyl group, and
the methoxypolyethylene glycol (meth)acrylate is a compound of formula [2]:

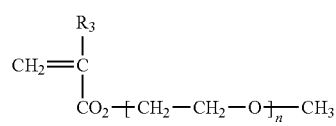

[2]

wherein $R_3$ represents a hydrogen atom or a methyl group, and n is 3,
wherein the (meth)acrylate copolymer is water-insoluble.

2. The (meth)acrylate copolymer of claim 1, wherein the alkyl (meth)acrylate and methoxypolyethylene glycol (meth)acrylate are copolymerized at a molar ratio of 30 to 90:10 to 70.

3. The (meth)acrylate copolymer of claim 1, wherein the (meth)acrylate copolymer is soluble in any of alcohols having 1 to 6 carbon atoms.

4. The (meth)acrylate copolymer of claim 1, wherein the (meth)acrylate copolymer has a glass transition temperature of −100 to 20° C.

5. The (meth)acrylate copolymer of claim 1, wherein the (meth)acrylate copolymer has a number average molecular weight of 2,000 to 200,000.

6. A method for producing the water-insoluble (meth)acrylate copolymer, of claim 1, the method comprises (a) copolymerizing hydrophobic (meth)acrylate and hydrophilic (meth)acrylate in a polymerization solvent that dissolves hydrophobic (meth)acrylate and hydrophilic (meth)acrylate to obtain water-insoluble (meth)acrylate copolymer, wherein the hydrophobic (meth)acrylate is a compound of formula [1]:

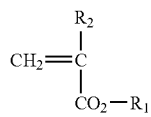

[1]

wherein $R_1$ represents an alkyl group or aralkyl group having 6 to 18 carbon atoms, and $R_2$ represents a hydrogen atom or a methyl group, and the hydrophilic (meth)acrylate is a compound of formula [2]:

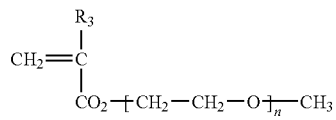

[2]

wherein $R_3$ represents a hydrogen atom or a methyl group, and n is 3, and (b) purifying the obtained water-insoluble (meth)acrylate copolymer to a purity of 90% by mol or more by reprecipitation.

7. The method of claim 6, wherein the polymerization solvent and monomers are present in a weight ratio of 20 to 90:80 to 10 when copolymerization of the monomers is initiated.

8. The method of claim 6, wherein the (meth)acrylate copolymer is purified by using a mixed solution of an alcohol having 1 to 10 carbon atoms and water as a reprecipitation poor solvent.

9. The method of claim 8, wherein the reprecipitation poor solvent is a mixture of an alcohol having 1 to 10 carbon atoms and water at a weight ratio of 0.1 to 99.9: 99.9 to 0.1.

10. The method of claim 6, wherein the (meth)acrylate copolymer solution and a reprecipitation poor solvent are mixed at a volume ratio of 1/5 to 1/10 and purification is performed when the copolymer is purified.

11. A medical device comprising a surface and the (meth)acrylate copolymer of claim 1, wherein the (meth)acrylate copolymer is present on at least a part of the surface.

* * * * *